US008353857B2

(12) United States Patent
Rosenberg

(10) Patent No.: US 8,353,857 B2
(45) Date of Patent: Jan. 15, 2013

(54) IMPLANTABLE MEDICAL DEVICE HAVING PRESSURE SENSORS FOR DIAGNOSING THE PERFORMANCE OF AN IMPLANTED MEDICAL DEVICE

(75) Inventor: Meir Rosenberg, Newton, MA (US)

(73) Assignee: Codman & Shurtleff, Inc., Raynham, MA (US)

( * ) Notice: Subject to any disclaimer, the term of this patent is extended or adjusted under 35 U.S.C. 154(b) by 1409 days.

(21) Appl. No.: 10/601,455

(22) Filed: Jun. 23, 2003

(65) Prior Publication Data

US 2004/0260229 A1 Dec. 23, 2004

(51) Int. Cl.
  *A61B 19/00* (2006.01)
(52) U.S. Cl. .............................. 604/9; 604/8
(58) Field of Classification Search ............... 604/6.1, 604/6.16, 7–10, 65–67, 264; 128/903, 905; 600/485, 486, 488; 607/60, 61
See application file for complete search history.

(56) References Cited

U.S. PATENT DOCUMENTS

| 4,206,761 | A |   | 6/1980  | Cosman             |
|-----------|---|---|---------|--------------------|
| 4,206,762 | A | * | 6/1980  | Cosman ...... 600/438 |
| 4,281,666 | A |   | 8/1981  | Cosman             |
| 4,281,667 | A |   | 8/1981  | Cosman             |
| 4,378,809 | A |   | 4/1983  | Cosman             |
| 4,385,636 | A |   | 5/1983  | Cosman             |
| 4,593,703 | A |   | 6/1986  | Cosman             |
| 4,595,390 | A |   | 6/1986  | Hakim et al.       |
| 4,598,579 | A |   | 7/1986  | Cummings et al.    |
| 4,615,691 | A |   | 10/1986 | Hakim et al.       |
| 4,653,508 | A |   | 3/1987  | Cosman             |
| 4,660,568 | A |   | 4/1987  | Cosman             |
| 4,772,257 | A |   | 9/1988  | Hakim et al.       |
| 4,776,838 | A |   | 10/1988 | Sainte-Rose et al. |
| 5,063,873 | A | * | 11/1991 | Zimmer ......... 118/414 |
| 5,431,057 | A |   | 7/1995  | Zimmer et al.      |
| 5,633,594 | A |   | 5/1997  | Okada              |
| 5,928,182 | A |   | 7/1999  | Kraus et al.       |
| 5,997,484 | A |   | 12/1999 | Sugahara           |

(Continued)

FOREIGN PATENT DOCUMENTS

EP     0982048 A    3/2000

(Continued)

OTHER PUBLICATIONS

Gross, M., et al., Optical Signal and Energy TGransmission for a Retina Implant, BMES-EMBS 1$^{st}$ Joint Conf., 1999, Atlanta USA.

(Continued)

*Primary Examiner* — Leslie Deak

(57) ABSTRACT

An implantable medical device that includes a housing, a valve disposed within the housing, a first pressure sensor disposed within the housing upstream of the valve, and a second pressure sensor disposed within the housing downstream of the valve. A CPU is disposed within the housing and is electrically connected to the first pressure sensor and the second pressure sensor. To communicate the measured pressure information to an external device, the CPU compares the pressure measured by the first pressure sensor to the pressure measured by the second pressure sensor and wirelessly communicates these compared pressures to an external device. Alternatively, the CPU may wirelessly communicate the absolute value of the pressure measured by the first pressure sensor and the second pressure sensor to the external device. Additionally, the CPU and sensors may be non-invasively powered using optical or acoustical methods.

45 Claims, 3 Drawing Sheets

U.S. PATENT DOCUMENTS

| | | | |
|---|---|---|---|
| 6,158,965 A | 12/2000 | Buttefield et al. | |
| 6,237,398 B1 | 5/2001 | Porat | |
| 6,248,080 B1* | 6/2001 | Miesel et al. | 600/561 |
| 6,416,291 B1 | 7/2002 | Butterfield et al. | |
| 6,470,213 B1* | 10/2002 | Alley | 607/41 |
| 6,585,677 B2* | 7/2003 | Cowan et al. | 604/9 |
| 6,783,499 B2* | 8/2004 | Schwartz | 600/486 |
| 6,926,670 B2* | 8/2005 | Rich et al. | 600/459 |
| 7,371,223 B2* | 5/2008 | Couvillon et al. | 604/9 |
| 2002/0156464 A1 | 10/2002 | Hooper et al. | |
| 2003/0004495 A1* | 1/2003 | Saul | 604/540 |

FOREIGN PATENT DOCUMENTS

| | | |
|---|---|---|
| EP | 1050264 A | 11/2000 |
| WO | WO 01/21066 | 3/2001 |

OTHER PUBLICATIONS

European Search Report EP 04253719 dated Jan. 17, 2005.
Steudel, et al.; English abstract for European Patent Application No. EP 0982048A; Dialog File No. 351; Accession No. 13001662; Derwent World Patents Index; 2005 Derwent Information Ltd.

\* cited by examiner

IMPLANTABLE MEDICAL DEVICE HAVING PRESSURE SENSORS FOR DIAGNOSING THE PERFORMANCE OF AN IMPLANTED MEDICAL DEVICE

BACKGROUND OF THE INVENTION

The present invention relates to an implantable medical device having pressure sensors for diagnosing the performance of the medical device. More specifically, the present invention relates to an implantable shunt having pressure sensors for diagnosing the performance of an implanted shunt by non-invasive techniques, such as telemetry.

DESCRIPTION OF THE RELATED ART

The present invention relates to an intracranial shunt that incorporates pressure sensors for measuring the pressure within the device and includes a device for communicating that information to an external device by telemetry.

Hydrocephalous is a condition in which the body, for any one of a variety of reasons, is unable to relieve itself of excess cerebral spinal fluid (CSF) collected in the ventricles of the brain. The excess collection of CSF in the ventricular space results in an increase in both epidural and intradural pressures. This, in turn, causes a number of adverse physiological effects, including compression of brain tissue, impairment of blood flow in the brain tissue, and impairment of the brain's normal metabolism. Treatment of a hydrocephalous condition frequently involves relieving the abnormally accumulated fluid volume with a shunt valve. The shunt valve is implanted in the body and, therefore, it is difficult to non-invasively verify the valve's performance.

A programmable valve, such as, for example, the CODMAN HAKIM Programmable Valve®, which is commercially available from Codman & Shurtliff, Inc. of Raynham, Mass., or the programmable shunt valve disclosed in U.S. Pat. Nos. 4,595,390, 4,615,691, 4772,257, and 5,928,182, the disclosures of which are hereby incorporated by reference in their entirety, are commonly referred to as the Hakim programmable valve. The Hakim valve described in these patents is a differential pressure valve with very precise opening pressures determined by the force exerted on a ruby ball in a ruby seat. The pressure at which the valve opens can be adjusted non-invasively by the clinician by means of an externally applied rotating magnetic field. The valve opening pressure is adjusted by varying the spring tension exerted on the ruby ball. Applying an external magnetic field to energize the soft magnet stator components of the valve initiates the adjustment cycle. The magnetic field causes the rotor to rotate about a central axis. As the stator polarity is cycled, the rotor (cam) moves to different positions to align with the stator. These components perform together as a stepping motor. The spring rides along the cam; as the cam rotates clockwise or counter-clockwise, the spring tension increases or decreases, respectively. Hakim programmable shunt valves utilize current practice that requires an x-ray to be taken after each valve adjustment to verify the new setting. The use of additional energy means to conventionally determine valve position, however, can often lead to undesirable complications. For instance, when magnetic fields are used for verifying valve position, metallic equipment within the clinical environment often interferes with the accuracy of information obtained through the use of these magnetic forces, leading to inaccurate readings.

Thus, there is a need in the art for a device that permits the surgeon to non-invasively verify the performance of the shunt valve. There is a further need in the art for a device that permits the surgeon to non-invasively verify the valve setting so that repeated exposure of the patient to magnetic or radiation energy is reduced or eliminated.

During use, shunt valves occasionally malfunction, but the reason for malfunction is not immediately known to the surgeon. One example of failure of the shunt valve could be occlusion of the drainage apertures within the ventricular catheter, thereby preventing fluid from entering into the valve housing mechanism. Another source of shunt failure could be a malfunction of the valve mechanism itself, or a blockage of the distal apertures in the drainage catheter. However, currently the only way for a medical professional to determine the source of failure is by using invasive medical techniques. Thus, there is a need in the art for a device which permits the surgeon to non-invasively determine the source of the shunt failure.

Therefore, it is an object of the present invention to provide such a device and a method for diagnosing the performance of an implanted medical device and to verify its valve setting.

SUMMARY OF THE INVENTION

These and other objects of the present invention are achieved with an implantable medical device that includes a housing, a valve disposed within the housing, a first pressure sensor disposed within the housing upstream of the valve, and a second pressure sensor disposed within the housing downstream of the valve. A CPU is disposed within the housing and is electrically connected to the first pressure sensor and the second pressure sensor. To communicate the measured pressure information to an external device, the CPU compares the pressure measured by the first pressure sensor to the pressure measured by the second pressure sensor and wirelessly communicates these compared pressures to an external device. Alternatively, the CPU may wirelessly communicate the absolute value of the pressure measured by the first pressure sensor and the second pressure sensor to the external device.

BRIEF DESCRIPTION OF THE DRAWING FIGURES

Further features and other objects and advantages of this invention will become clear from the following detailed description made with reference to the accompanying drawings illustrating in a schematic and non-limiting way an implantable medical device having pressure sensors for diagnosing the performance of an implanted medical device according to the invention and in which.

DETAILED DESCRIPTION OF THE CURRENTLY PREFERRED EXEMPLARY EMBODIMENT

Figure 1:
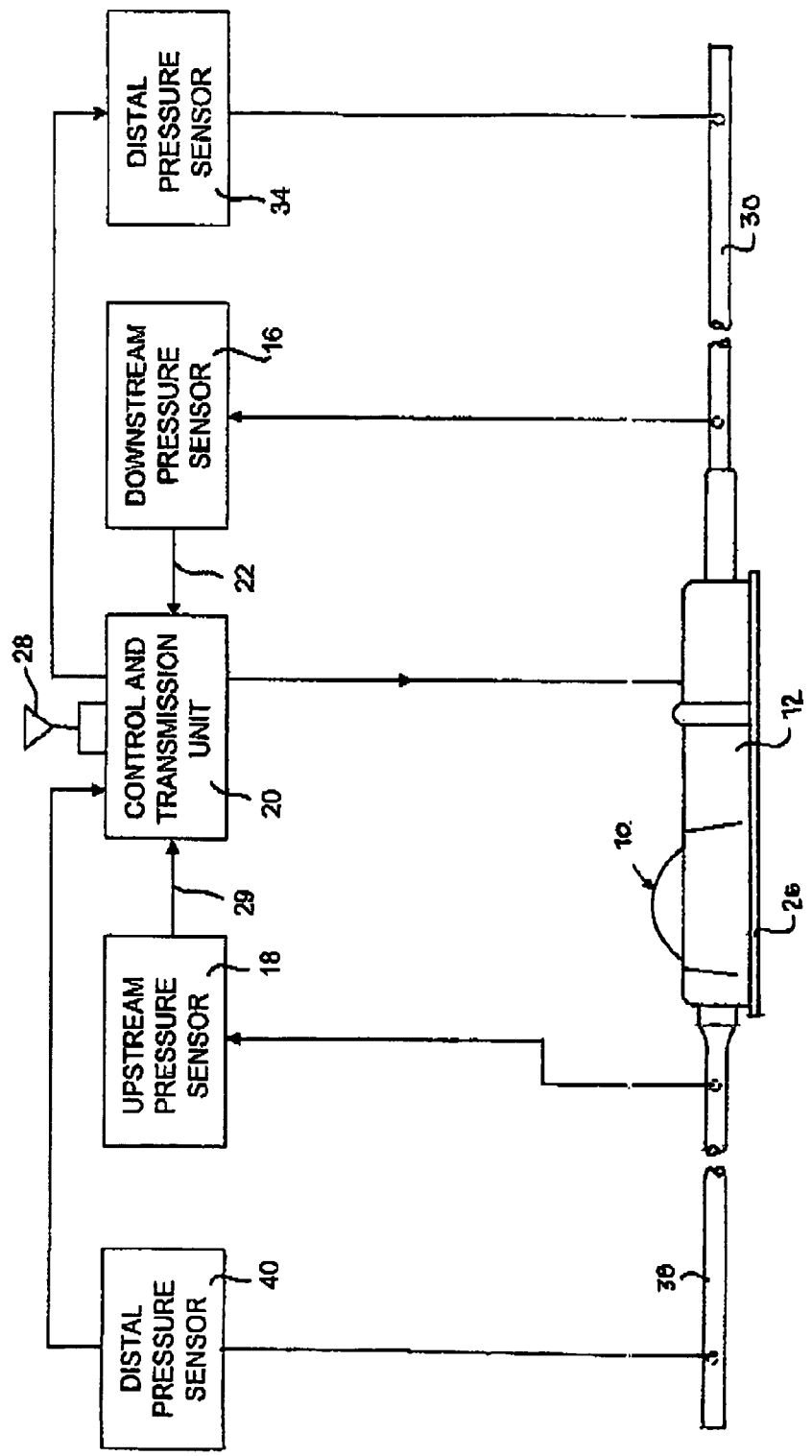
FIG. 1 is a side view of an implantable shunt system in accordance with the present invention.
Figure 2:
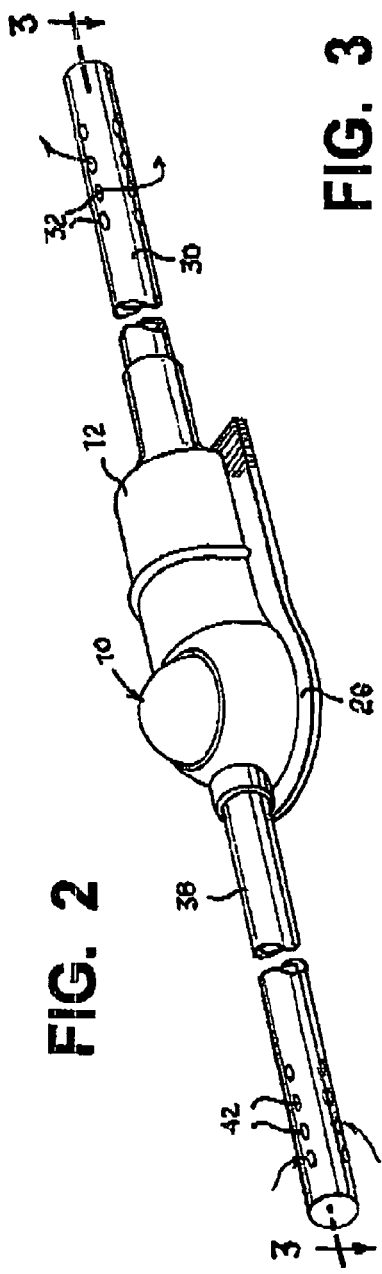
FIG. 2 is a perspective view of the implantable shunt system shown in FIG. 1.
Figure 3:
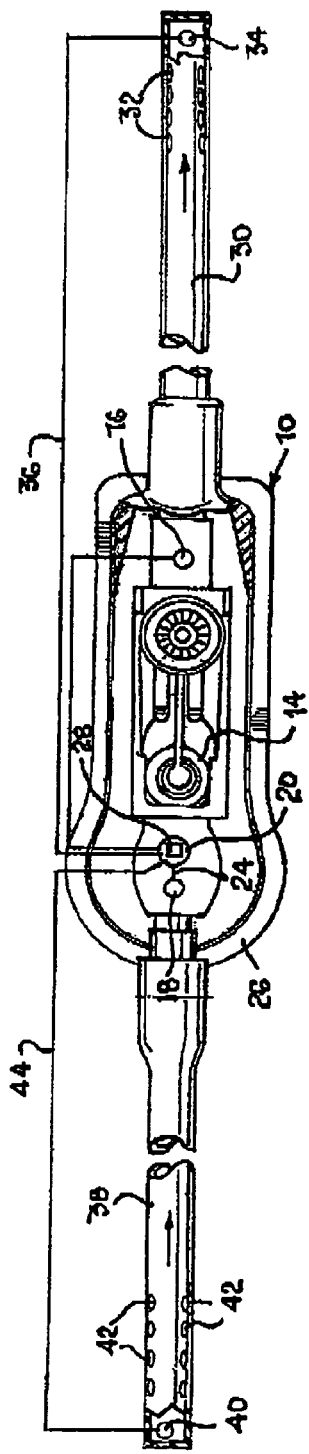
FIG. 3 is a partial top sectional view of the shunt shown in FIG. 1.
Figure 4:
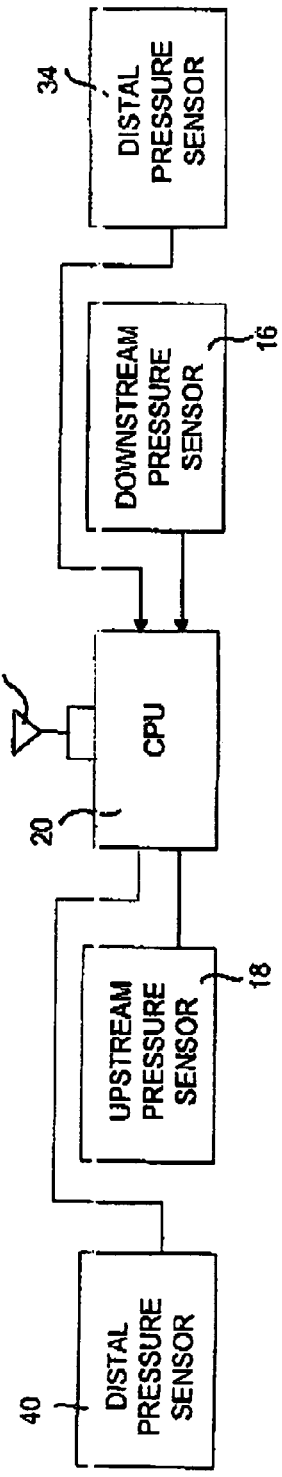
FIG. 4 is a schematic showing the communications between the pressure sensors and the CPU.

Referring now to FIGS. 1-4, an implantable shunt system (10) in accordance with the present invention, is illustrated. Device (10) includes a housing (12), and a valve mechanism (14) disposed within housing (12). Valve (14) is preferably an Hakim-type programmable valve, as is known in the art. See, for example, U.S. Pat. No. 5,928,182 to Kraus et al., the disclosure of which is hereby incorporated by reference. Of course, other pressure relief valves may be utilized within housing (12), as desired by the user. As illustrated in FIG. 4, a first pressure sensor (16) is disposed within housing (12) and downstream of valve (14). A second pressure sensor (18) is disposed within housing (12) upstream of valve (14). A central processing unit ("CPU") (20) is disposed within housing (12) and is electrically connected to the first pressure sensor (16) by line (22) and to second pressure sensor (18) by line (24). In practice, pressure sensors (16), (18) and CPU (20) may lie on a common ceramic substrate or PC board (26), with lines (22), (24) also lying upon PC board (26). CPU (20) preferably includes an antenna (28) for wireless communicating with an external device by telemetry in a manner known to those skilled in the art. CPU (20) includes a processor for calculating the differential pressure between the first pressure sensor (16) and the second pressure sensor (18).

A first catheter (38) is fluidly connected to housing (12). First catheter (38) is preferably a ventricular catheter, which can be placed within the ventricles of the brain to drain excess fluid therefrom. Catheter (38) includes a plurality of drainage apertures (42). Cerebral spinal fluid is preferably received within apertures (42) and is drained therefrom when the pressure difference between the ventricles and the drainage site (peritoneum or right atrium) exceeds the differential pressure set by valve (14). Disposed within first catheter (38), preferably distally with respect to apertures (32), is a third pressure sensor (42). Third pressure sensor (40) is electrically connected to CPU (20) by line (44). Line (44) is illustrated schematically in FIG. 3 as being external to the catheter, but, in practice, line (44) will preferably run internally or within catheter (38) directly to PC board (26) and eventually to the CPU (20). Similarly, a drainage catheter (30) is fluidly connected to housing (12) to drain fluid from the ventricles to another portion of the body, in a manner known in the art. A fourth pressure sensor (34) is disposed within drainage catheter (30), preferably distally with respect to the plurality of drainage apertures (32). Fourth pressure sensor (34) is electrically connected to CPU (20) by line (36). As with line (44), line (36) is also preferably disposed within or internally within catheter (30) and is electrically connected to PC board (26) and eventually to CPU (20).

CPU (20) can measure the differential pressure or absolute pressure of any pressure sensor (16), (18), (34), (40). This information, which is preferably communicated to an external device by telemetry may be used by a medical professional to determine if the shunt is working properly or not. For example, if the differential pressure between third pressure sensor (40) and second pressure sensor (18) is high, [meaning that the pressure detected by sensor (40) is relatively high, whereas the pressure detected by sensor (18) is relatively low], then the operator will know that there is a blockage within first catheter (38). Similarly, based on the pressures measured by sensors (18) and (16) immediately both upstream and downstream of the valve (14), one can determine if the valve is malfunctioning. For example, if valve (14) is set to open at 100 mm water, and the differential pressure across the valve is higher than 100 mm water (i.e., the valve set pressure), then this is an indication that the valve may not be operating properly. When the measured pressure exceeds the valve set pressure, this is an indication of a potential valve failure. In another example, if the pressure sensed from all four pressure sensors is relatively high, it is an indication that the drainage catheter (30) is blocked and no fluid is getting out of or being drained from this catheter (30). Finally, if the differential pressure between sensor (16) and fourth pressure sensor (34) is relatively low, then one will know that the distal catheter is working properly. However, if this differential pressure is relatively high, then one can deduce that there may be an occlusion in the drainage catheter (30) somewhere between these two sensors (16, 34).

Figure 5:
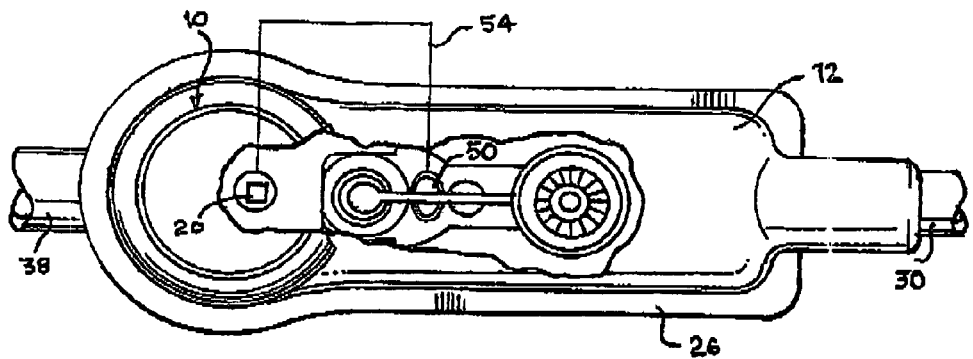
FIG. 5 is a partial top sectional view of the shunt system in accordance with another embodiment of the present invention.
Figure 6:
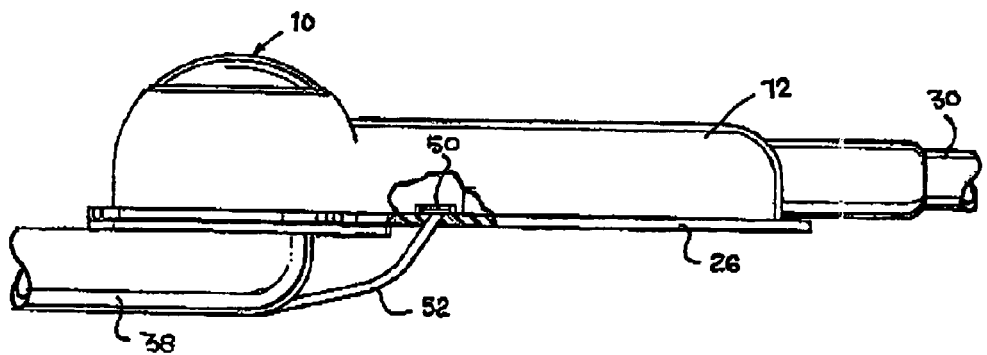
FIG. 6 is a side view of the shunt system shown in FIG. 5.

Referring now to FIGS. 5 and 6, another embodiment of the present invention is illustrated. In this embodiment, many of the elements are identical to the embodiment shown in FIGS. 1-4 and described above. Thus, for the sake of brevity in the disclosure, only those elements that differ will be described. In this embodiment a membrane (50), which forms a barrier between one side of valve (14) and the other side, acts as a differential pressure sensor and can replace, if desired, first pressure sensor (16) and second pressure sensor (18). As illustrated in FIG. 6, the lower surface of membrane (50) is exposed to fluid pressure upstream of the valve by a fluid conduit (52), whereas the upper surface of membrane (50) is exposed to fluid pressure downstream of the valve. Of course, the terms "upper" and "lower" are used herein with reference to the drawing figures to ease the description of the present invention, and are not intended to limit the scope of the present invention. In use, the portion of the housing described as upper, may in fact be lower, and vice versa.

Membrane (50) is electrically connected to CPU (20) by line (54). Line (54) is illustrated schematically in FIG. 6 as being external to the shunt housing, but, in practice, line (54) will preferably run internally atop of the PC board (26) within the shunt housing directly to the CPU (20). One skilled in the art will recognize that membrane (50) can be of conventional design, such as, for example, the ones disclosed in U.S. Pat. Nos. 5,431,057 and 5,633,594, the disclosures of which are hereby incorporated by reference in their entirety. Based upon the position of membrane (50), the differential pressure across the valve can be determined. Thus, one can determine if the valve is malfunctioning based upon the signal received from membrane (50). For example, if valve (14) is set to open at 100 mm water, and the differential pressure across the valve is higher than 100 mm water (i.e., the valve set pressure), then this is an indication that the valve may not be operating properly. When the measured pressure exceeds the valve set pressure, this is an indication of a potential valve failure.

In each of the above described embodiments, the sensors have been described as communicating directly with an internal CPU (20). However, each sensor could communicate to an external device by telemetry. The external device would then perform the function of CPU (20). Alternatively, the CPU may transmit the individual pressure reading from each sensor and the external receiver may perform the necessary calculations.

Thus, a method for diagnosing the performance of an implanted medical device in accordance with the present invention includes comparing the pressure measured by the first pressure sensor to the pressure measured by the second pressure sensor or comparing the pressure measured by any one of the first, second, third or fourth pressure sensors to any one of the other of the first, second, third or fourth pressure sensors and wirelessly communicating these compared pressures to an external device. Alternatively, the CPU may wirelessly communicate the absolute value of the pressure measured by any one of the first, second, third or fourth pressure sensors to the external device. The CPU and sensors are preferably non-invasively powered by the external device using RF telemetry. However, the CPU and sensors may be non-invasively powered using optical or acoustical methods. The sensors could also directly communicate with the external device using acoustic waves, thereby eliminating the need of the CPU. Such sensors are currently available from Remon Medical Technologies, Ltd, 7 Halamish St, Caesaria Industrial Park, 38900, Israel. Alternatively, as one skilled in the art will recognize, the CPU and sensors may communicate with an external device using RF or optics. An example of an optical signal and energy transmission device is disclosed in Optical Signal and Energy Transmission for a Retina Implant, by M. Gross et al. and published in BMEW-EMBS $1^{st}$ Joint conference, 1999, Atlanta, USA, the disclosure of which is hereby fully incorporated by reference in its entirety.

Having described the presently preferred exemplary embodiment of an implantable medical device having pressure sensors for diagnosing the performance of the medical device in accordance with the present invention, it is believed that other modifications, variations and changes will be suggested to those skilled in the art in view of the teachings set forth herein. It is, therefore, to be understood that all such modifications, variations, and changes are believed to fall within the scope of the present invention as defined by the appended claims.

The invention claimed is:

1. An implantable medical device comprising:
a housing;
a valve disposed within said housing;
a non-invasively wirelessly powered first pressure sensor disposed within said housing and upstream of said valve;
a non-invasively wirelessly powered second pressure sensor disposed within said housing and downstream of said valve; and
a non-invasively wirelessly powered CPU disposed within said housing and being operatively connected to said first pressure sensor and said second pressure sensor.

2. The device according to claim 1, wherein the CPU is electrically connected to said first pressure sensor and said second pressure sensor.

3. The device according to claim 2, wherein the CPU has means for wirelessly communicating is adapted to communicate within an external device.

4. The device according to claim 3, wherein the CPU has means for calculating a differential pressure between the first pressure sensor and the second pressure sensor.

5. The device according to claim 1, wherein the CPU has means for calculating a differential pressure between the first pressure sensor and the second pressure sensor.

6. The device according to claim 1, further comprising a first catheter fluidly connected to said housing, and a third pressure sensor disposed within said first catheter.

7. The device according to claim 6, wherein said third pressure sensor is operatively connected to said CPU.

8. The device according to claim 7, wherein said first catheter is fluidly connected to said housing upstream of said valve.

9. The device according to claim 8, wherein the CPU has means for wirelessly communicating is adapted to communicate with an external device.

10. The device according to claim 9, wherein the CPU has means for calculating a differential pressure between the first pressure sensor and the second pressure sensor, and for calculating a differential pressure between the third pressure sensor and at least one of the first pressure sensor and the second pressure sensor.

11. The device according to claim 10, further comprising a second catheter fluidly connected to said housing, and a fourth pressure sensor disposed within said second catheter.

12. The device according to claim 11, wherein said fourth pressure sensor is electrically connected to said CPU.

13. The device according to claim 12, wherein said second catheter is fluidly connected to said housing downstream of said valve.

14. The device according to claim 13, wherein the CPU has means for calculating a differential pressure between the first pressure sensor and the second pressure sensor and for calculating a differential pressure between the fourth pressure sensor and at least one of the first pressure sensor, the second pressure sensor and the third pressure sensor.

15. The device according to claim 1, wherein the CPU has means for being is non-invasively powered using RF.

16. The device according to claim 1, wherein the CPU has means for being is non-invasively powered using acoustics.

17. The device according to claim 1, wherein the CPU has means for being is non-invasively powered using optics.

18. The device according to claim 1, wherein said first pressure sensor and said second pressure sensor are disposed on a common substrate.

19. An implantable medical device comprising:
a housing;
a valve disposed within said housing;
a non-invasively wirelessly powered first pressure sensor disposed within said housing and upstream of said valve;
a non-invasively wirelessly powered second pressure sensor disposed within said housing and downstream of said valve; and
a non-invasively wirelessly powered CPU being operatively connected to said first pressure sensor and said second pressure sensor.

20. The implantable medical device according to claim 19, wherein said CPU is disposed within said housing.

21. The implantable medical device according to claim 19, wherein said CPU is disposed external to said housing.

22. The device according to claim 19, wherein said first pressure sensor and said second pressure sensor are disposed on a common substrate.

23. The device according to claim 22, wherein said CPU is disposed on said common substrate.

24. A method for diagnosing the performance of an implanted medical device, wherein the implanted medical device has:
a housing;
a valve disposed within said housing;
a non-invasively wirelessly powered first pressure sensor disposed within said housing and upstream of said valve;
a non-invasively wirelessly powered second pressure sensor disposed within said housing and downstream of said valve; and
a non-invasively wirelessly powered CPU disposed within said housing and being operatively connected to said first pressure sensor and said second pressure sensor,
the method comprising the steps of:
comparing the pressure measured by the first pressure sensor to the pressure measured by the second pressure sensor; and
wirelessly communicating the compared pressures to an external device.

25. The method according to claim 24, wherein the device further has a first catheter fluidly connected to said housing, and a third pressure sensor disposed within said first catheter, said method further comprising the steps of:

comparing the pressure measured by the third pressure sensor to one of the pressure measured by the first pressure sensor and second pressure sensor.

26. The method according to claim 25, wherein the device further comprising a second catheter fluidly connected to said housing, and fourth pressure sensor disposed within said second catheter, said method further comprising the step of:

comparing the pressure measured by the fourth pressure sensor to one of the pressure measured by the first pressure sensor, the second pressure sensor and third pressure sensor.

27. A method of diagnosing the performance of an implanted medical device wherein the implanted medical device has:

a housing;
a valve disposed within said housing;
a non-invasively wirelessly powered first pressure sensor disposed within said housing and upstream of said valve;
a non-invasively wirelessly powered second pressure sensor disposed within said housing and downstream of said valve; and
a non-invasively wirelessly powered CPU disposed within said housing and being operatively connected to said first pressure sensor and said second pressure sensor,
the method comprising the steps of:
determining by the CPU, the pressure detected by the first pressure sensor;
determining by the CPU, the pressure detected by the second pressure sensor; and
wirelessly communicating the determined pressures to an external device.

28. An implantable medical device comprising:
a housing;
a valve disposed within said housing;
a non-invasively wirelessly powered differential pressure sensor disposed within said housing ; and
a non-invasively wirelessly powered CPU disposed within said housing and being electrically connected to said differential pressure sensor.

29. The device according to claim 28 wherein the CPU has means for wirelessly communicating is adapted to communicate within an external device.

30. The device according to claim 28, further comprising a first catheter fluidly connected to said housing, and a non-invasively wirelessly powered second pressure sensor disposed within said first catheter.

31. The device according to claim 30, wherein said second pressure sensor is operatively connected to said CPU.

32. The device according to claim 31, wherein said first catheter is fluidly connected to said housing upstream of said valve.

33. The device according to claim 32, wherein the CPU has means for wirelessly communicating is adapted to communicate within an external device.

34. The device according to claim 33, further comprising a second catheter fluidly connected to said housing, and a third pressure sensor disposed within said second catheter.

35. The device according to claim 34, wherein said third pressure sensor is operatively connected to said CPU.

36. The device according to claim 35, wherein said second catheter is fluidly connected to said housing downstream of said valve.

37. The device according to claim 28, wherein the CPU has means for being is non-invasively powered using RF.

38. The device according to claim 28, wherein the CPU has means for being is non-invasively powered using acoustics.

39. The device according to claim 28, wherein the CPU has means for being is non-invasively powered using optics.

40. The device according to claim 28, wherein said differential pressure sensor and said CPU are disposed on a common substrate.

41. A method of diagnosing the performance of an implanted medical device wherein the implanted medical device has:

a housing;
a valve disposed within said housing;
a non-invasively wirelessly powered differential pressure sensor disposed within said housing; and
a non-invasively wirelessly powered CPU disposed within said housing and being electrically connected to said differential pressure sensor,
the method comprising the steps of:
determining by the CPU, the pressure detected by the differential pressure sensor; and
wirelessly communicating the determined pressure to an external device.

42. A method for diagnosing the performance of an implanted medical device, wherein the implanted medical device has:

a housing;
a valve disposed within said housing;
a non-invasively wirelessly powered first pressure sensor disposed within said housing and upstream of said valve; and
a non-invasively wirelessly powered second pressure sensor disposed within said housing and downstream of said valve;
the method comprising the steps of:
wirelessly communicating a signal representative of the pressure detected by the first pressure sensor to an external device;
wirelessly communicating a signal representative of the pressure detected by the second pressure sensor to an external device; and
comparing the pressure detected by the first pressure sensor to the pressure detected by the second pressure sensor with the external device.

43. A method for diagnosing the performance of an implanted medical device, wherein the implanted medical device has:

a housing;
a valve disposed within said housing;
a non-invasively wirelessly powered first pressure sensor disposed within said housing and upstream of said valve; and
a non-invasively wirelessly powered second pressure sensor disposed within said housing and downstream of said valve;
the method comprising the steps of:
generating a signal from the first pressure sensor;
generating a signal from the second pressure sensor;
comparing the signals from the first pressure sensor and the second pressure sensor;

generating a signal representative of the difference in pressure between the pressure measured by the first pressure sensor and the pressure measured by the second pressure sensor;

wirelessly communicating the signal representative of the difference in pressure to an external device.

44. An implantable medical device comprising:

a housing;

a valve disposed within said housing;

a non-invasively wirelessly powered first pressure sensor disposed within said housing and upstream of said valve; and a non-invasively wirelessly powered second pressure sensor disposed within said housing and downstream of said valve.

45. The device according to claim 44, wherein said first pressure sensor and said second pressure sensor are disposed on a common substrate.

* * * * *